United States Patent [19] [11] 4,250,328
Fujita et al. [45] Feb. 10, 1981

[54] METHOD FOR SEPARATION OF AN ESTER FROM A REACTION MIXTURE

[75] Inventors: Kiyoshi Fujita; Yukiyoshi Ito, both of Yokkaichi; Shigeru Kamimori, Matsuzaka, all of Japan

[73] Assignee: Kyowa Yuka Co., Ltd., Tokyo, Japan

[21] Appl. No.: 9,793

[22] Filed: Feb. 6, 1979

[30] Foreign Application Priority Data

Feb. 8, 1978 [JP] Japan .................................. 53-12299

[51] Int. Cl.³ ........................ C07C 67/48; C07C 69/54
[52] U.S. Cl. .................................... 560/205; 560/218; 560/248; 560/265; 203/60; 203/66; 203/DIG. 6; 203/DIG. 19
[58] Field of Search ............... 560/205, 218, 231, 248, 560/265; 203/DIG. 6

[56] References Cited

U.S. PATENT DOCUMENTS

| | | | |
|---|---|---|---|
| 3,404,175 | 10/1968 | Mercier | 560/231 |
| 3,431,181 | 3/1969 | Bouniot | 560/218 |
| 3,458,561 | 7/1969 | Kautter et al. | 560/205 |
| 3,776,947 | 12/1973 | Shimizu et al. | 560/205 |
| 4,076,950 | 2/1978 | Stewart et al. | 560/218 |

OTHER PUBLICATIONS

Kirk-Othmer "Encyclopedia of Chemical Technology", 2nd Ed. (1966), vol. 8, p. 367.

Primary Examiner—Natalie Trousof
Assistant Examiner—L. Hendriksen
Attorney, Agent, or Firm—Fitzpatrick, Cella, Harper & Scinto

[57] ABSTRACT

An improved method for separating an ester formed in a reaction mixture is disclosed. The method comprises controlling the ratio of organic acid and alcohol utilized and the removal of unreacted alcohol as an alcohol-ester azeotrope.

3 Claims, 1 Drawing Figure

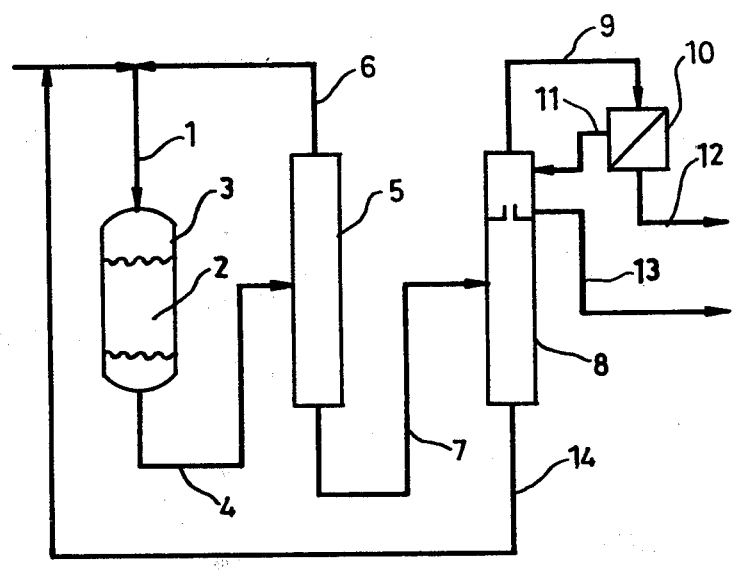

METHOD FOR SEPARATION OF AN ESTER FROM A REACTION MIXTURE

BACKGROUND OF THE INVENTION

The present invention relates generally to a method for separation of an ester such as methyl iso-butyrate or methyl methacrylate from a reaction mixture in which the ester is formed by reaction of an organic acid with an alcohol.

In the known industrial method, an ester is generally produced by reacting alcohol with an equimolar amount of organic acid in the presence of a suitable catalyst. The thus produced ester is then purified by fractional distillation. This reaction however suffers from the disadvantage that it is never complete and must be closely controlled in order to avoid formation of by-products. Although the reaction theoretically should be complete, even under ideal conditions, the reaction mixture usually contains a substantial proportion of unreacted alcohol and organic acid which must be separated from the ester. The separation of the ester from the reactants by simple fractional distillation is rendered difficult owing to the formation of alcohol-ester or ester-water azeotropes.

As a result of studies on the separation of esters from the reaction mixture, it has now been found that the ester may be readily separated by reacting an alcohol with an excess amount of organic acid based on that of alcohol, and removing the unreacted alcohol from the reaction mixture as an alcohol-ester azeotrope.

SUMMARY OF THE INVENTION

Broadly the present invention is directed to the separation of an ester particularly methyl iso-butyrate and methyl methacrylate from a reaction mixture comprising ester, alcohol, organic acid and water. More specifically, this invention is directed to a method for the separation of ester from a reaction mixture comprising ester, alcohol, organic acid and water which comprises reacting an alcohol with an excess amount of organic acid based on that of alcohol, removing the unreacted alcohol in the reaction mixture as an alcohol-ester azeotrope and recovering the ester from the mixture which is comprised of ester, organic acid and water and which is substantially free of alcohol.

The present invention is based on the following principle.

There are four components, i.e. ester, alcohol, organic acid and water in the reaction mixture obtained by reaction of alcohol with organic acid. When the reaction mixture is subjected to distillation, an alcohol-ester azeotrope and an ester-water azeotrope may be formed. Among the four components and two azeotropes for the two esters described above, the alcohol-ester azeotrope has the lowest boiling point, the next is the ester-water azeotrope, the third is the ester, and the fourth is the organic acid. Therefore, when the reaction mixture is subjected to distillation, firstly, alcohol-ester azeotrope is formed and is distilled away. After all of the alcohol is distilled away, an ester-water azeotrope is formed.

The ester is readily separated from a mixture which is comprised of ester, water and organic acid and which is substantially free of alcohol.

In order to obtain an ester in a high yield according to the above-described method, the amount of the alcohol contained in the reaction mixture must be minimized; and therefore, in the reaction of alcohol with organic acid, an excess amount of organic acid must be used to that of alcohol.

DETAILED DESCRIPTION OF THE INVENTION

The accompanying drawing is a process flow diagram illustrating a preferred continuous method for carrying out the invention.

With reference to the drawing, alcohol and organic acid are fed, by means of connection 1, to reactor 3 packed with a cation exchange resin 2 where an ester is formed by reaction of the organic acid with the alcohol. A reaction mixture from the reactor which consists of ester, alcohol, organic acid and water is fed, by means of connection 4, to a first distillation column 5 where an overhead fraction of alcohol-ester azeotrope is formed and is returned, by means of connection 6, to reactor 3. The base fraction from distillation column 5 which is a mixture of ester, organic acid and water and which is substantially free of alcohol is fed, by means of connection 7, to a second distillation column 8 where an overhead fraction of ester-water azeotrope is formed and is passed, by means of connection 9, to separator 10. The ester layer, separated in separator 10, is refluxed, by means of connection 11, to column 8. The water layer is discharged by means of connection 12.

The desired ester is recovered, as a side cut, by means of connection 13 from the second distillation column 8. The base fraction from column 8, which consists of organic acid is returned to reactor 3 by means of connection 14.

According to the present invention, the reaction of organic acid with alcohol is carried out in an excess amount of organic acid to that of alcohol in the presence of a suitable catalyst. The more organic acid there is, the smaller the amount of unreacted alcohol. However, if the amount of organic acid is too excessive, the process becomes uneconomical because of the increase of circulation of organic acid. Therefore, the amount of organic acid is usually 1.5–10 moles, preferably 2–4 moles per 1 mole of alcohol. In accordance with the invention, the amount of unreacted alcohol in the reaction mixture should be less than 4.0% (W/W) preferably less than 2.0% (W/W).

As the catalyst for esterification, any catalyst may be used so long as it catalyzes the reaction of organic acid with alcohol. Examples of suitable catalysts are mineral acids such as sulfuric acid, phosphoric acid, etc., organic acids such as benzene sulfonic acid, p-toluene sulfonic acid, etc. and cation exchange resin, etc.

The reaction is carried out by the known reaction systems according to the type of catalyst. When a homogeneous catalyst such as a solution is utilized, any reactor may be used. When a solid type catalyst is utilized, the reaction is preferably carried out in a fluidized bed or fixed bed.

When the reaction temperature is low, the rate of reaction is slow and it takes much time to reach the equiliblium. On the other hand, when it is high, by-products are produced. Therefore, the reaction is carried out at a temperature of 30°–120° C. preferably at 50°–90° C.

When raw materials or products are liable to be polymerized in the reaction or distillation steps, a polymerization inhibitor such as hydroquinone, hydroquinone mono-methyl ether, or the like may be added to the reactor or the distillation column.

After the completion of the reaction, the reaction mixture is neutralized with an alkaline solution such as sodium hydroxide, etc. and is subjected to filtration for removing the catalyst. When a cation exchange resin is utilized as the catalyst, neutralization is unnecessary. Similarly, when the reaction is carried out in a fixed bed system, filtration is unnecessary.

The filtrate is then introduced to the first distillation column which is controlled at atmospheric or reduced pressure and is subjected to distillation to form an alcohol-ester azeotrope. The temperature of the column is automatically determined by the column pressure and the components of the solution in the column. The azeotropic mixture is distilled away and is recycled to the reactor, if desired. In this case, the amount of ester utilized for making the azeotropic mixture with unreacted alcohol in the first distillation column is small because of the small amount of unreacted alcohol.

The desired ester is recovered from the base fraction of the column which is a mixture of ester, water and organic acid according to known methods. For example, the base fraction is fed to the second distillation column where an ester-water azeotrope is formed in the column as an overhead fraction. The azeotropic mixture is removed to a separator where an ester layer and a water layer are formed. The ester layer is refluxed to the top of the second distillation column. The desired ester is then recovered and isolated as a side cut flow of the overhead fraction in the second distillation column, in high purity. The base fraction consisting of organic acid is usually recycled to the reactor.

Any part or all of the separation and purification system above described can be operated at atmospheric pressure or under a vacuum. The second distillation column can be operated at any convenient reflux ratio and the refux ratio will vary depending on the components of the mixture introduced therein for separation.

The proper reflux ratio for various mixtures can be readily determined by those skilled in the art. Usually, a reflux ratio varying from about 2:1 to 10:1 can be employed satisfactory.

Certain specific embodiments of the present invention are illustrated by the following representative examples.

EXAMPLE 1

In this example, methyl iso-butyrate is synthesized from iso-butyric acid and methanol in a reactor packed with 100 ml of a cation exchange resin, namely PK 220 (trade mark of Mitsubishi Chemical Industries, Ltd.), as the catalyst.

Iso-butyric acid, at a rate of 245.8 g/h, methanol at a rate of 40.1 g/h, and a mixture of 70% methanol, 29% methyl iso-butyrate and 1% water at a rate of 6.6 g/h are fed to the reactor. The molar ratio of iso-butyric acid to methanol at the inlet of the reactor is maintained at 2.0. The reaction is carried out at a temperature of 90° C. and at a pressure of 4Kg/cm$^2$ Gage of nitrogen gas for suppressing vaporization of the reaction product. Under these conditions, the reaction proceeds quantitatively i.e., most of the alcohol is converted to ester, and the yield of methyl iso-butyrate is 89.7% based on methanol supplied.

The reaction mixture containing 1.6% methanol, 44.4% methyl iso-butyrate, 7.7% water and 46.3% iso-butyric acid is separated in the manner described above with reference to the drawing. More specifically, the reaction mixture is introduced to a first distillation column which is maintained at atmospheric pressure. An overhead fraction containing 70% methanol, 29% methyl iso-butyrate and 1% water and having a boiling point of 64° C. is recycled to the reactor at a rate of 6.6 g/h. The base fraction of the column, having a temperature of 100° C., is fed to a second distillation column having a side-cut outlet, which is maintained at atmospheric pressure. An azeotropic mixture of methyl iso-butyrate and water having a boiling point of 78° C., produced as an overhead fraction in the second column is removed to a separator. The ester layer formed in the separator is refluxed back to the second distillation column; and the water layer, containing 1.4% methyl iso-butyrate, is discharged out of the system at a rate of 22.7 g/h. The fraction of methyl iso-butyrate having a temperature of 92° C. is taken from the side cut outlet at a rate of 127.8 g/h. The purity of the methyl iso-butyrate is 99.8% and the rest is water.

Iso-butyric acid having a temperature of 158° C. is taken from the base of the column at a rate of 135.5 g/h and recycled to the reactor.

EXAMPLE 2

In this example, methyl methacrylate is synthesized from methanol and methacrylic acid in a manner similar to that described in Example 1.

A mixture containing 11% methanol, 0.2% methyl methacrylate, 0.02% water and 88.8% methacrylic acid is fed to the reactor at a rate of 300 g/h. Hydroquinone as a polymerization inhibitor is also fed to the reactor at a ratio of 100 ppm based on the total raw materials. The reaction is carried out at a temperature of 77° C. and at a pressure of 2 Kg/cm$^2$ Gage with nitrogen gas. The reaction proceeds quantitatively and the yield of methyl methacrylate is 92.9% based on the amount of supplied methanol.

The reaction mixture containing 0.8% methanol, 32.2% methyl methacrylate, 5.8% water and 61.2% methacrylic acid is introduced to a first distillation column which is maintained at a pressure of 400 mmHg. An overhead fraction containing 78.0% methanol, 21.0% methyl methacrylate and 1.0% water and having a boiling point of 48° C. is recycled to the reactor at a rate of 3.0 g/h. The base fraction, having a temperature of 100° C., is taken from the base of the column and removed to a second distillation column which is maintained at a pressure of 200 mmHg.

An overhead fraction, having a boiling point of 49° C. and consisting of methyl methacrylate and water is removed to a separator to form an ester layer and a water layer. The ester layer is refluxed to the top of the second distillation column and the water layer, containing 1.5% methyl methacrylate, is discharged out of the system at a rate of 17.4 g/h.

The fraction of methyl methacrylate having a temperature of 62° C. is taken from the side cut outlet at a rate of 95.9 g/h. The purity of the methyl methacrylate is 99.8% and the rest is water. The base fraction is taken from the base of the column at a rate of 183.7 g/h and recycled to the reactor.

What is claimed is:

1. In a method for producing an ester selected from the group consisting of methyl isobutyrate and methyl methacrylate by reacting methanol with the corresponding organic acid, the improvement which comprises: reacting the methanol with an excess amount of the corresponding organic acid based on the amount of methanol; removing the unreacted methanol from the reaction mixture as a methanol-ester azeotrope; distilling the resulting mixture of ester, water and organic acid in a distillation column to form an ester-water azeotrope; separating said ester-water azeotrope to form an ester layer and a water layer; refluxing said ester layer to said distillation column; and isolating the ester as a side cut flow of an overhead fraction from said distillation column.

2. A method according to claim 1, wherein said reaction is carried out in a molar ratio of 10 to 1.5, moles organic acid per mole of methanol.

3. A method according to claim 1, wherein said reaction mixture contains methanol in an amount of less than 4.0% (W/W).

* * * * *